United States Patent
Wizel et al.

(10) Patent No.: US 7,517,993 B2
(45) Date of Patent: Apr. 14, 2009

(54) PIOGLITAZONE HYDROCHLORIDE

(75) Inventors: Shlomit Wizel, Petah Tiqva (IL); Serguei Finogueev, Qiriat Arbaa (IL); Jean Hildesheim, Mazkeret Batya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 149 days.

(21) Appl. No.: 11/588,497

(22) Filed: Oct. 27, 2006

(65) Prior Publication Data

US 2007/0043094 A1    Feb. 22, 2007

Related U.S. Application Data

(62) Division of application No. 10/256,437, filed on Sep. 27, 2002, now Pat. No. 7,135,485.

(60) Provisional application No. 60/326,112, filed on Sep. 28, 2001.

(51) Int. Cl.
*C07D 417/10* (2006.01)
*A61K 31/4436* (2006.01)

(52) U.S. Cl. .................. 546/269.7; 514/342
(58) Field of Classification Search ............ 514/342; 546/269.7
See application file for complete search history.

(56) References Cited

U.S. PATENT DOCUMENTS

| 4,687,777 A | 8/1987 | Meguro et al. |
| 5,585,495 A | 12/1996 | Huber |
| 5,700,820 A | 12/1997 | Vyas et al. |
| 5,952,509 A | 9/1999 | Saito et al. |

FOREIGN PATENT DOCUMENTS

WO    WO 0228857    9/2001

OTHER PUBLICATIONS

G. M. Wall, "Pharmaceutical Applications of Drug Crystal Studies," Pharmaceutical Manufacturing, vol. 3, No. 2, Feb. 1986, pp. 33-42.
J. Haleblian and W. McCrone, "Pharmaceutical Applications of Polymorphism," Journal of Pharmaceutical Sciences, vol. 58, No. 8, Aug. 1969, pp. 911-929J. Pharm. Sci., 58,911 (1969).
J.K. Haleblian, "Characterization of Habits and Crystalline Modification of Solids and Their Pharmaceutical Applications," Journal of Pharmaceutical Sciences, vol. 64, No. 8, Aug. 1975, pp. 1269-1288.
Concise Encyclopedia Chem. (1994), Walter de Gruyter, Berlin, New York, p. 872-873.
A. Maureen Rouchi, Chemical & Engineering News, Feb. 24, 2003, p. 32-35.

*Primary Examiner*—Rei-Tsang Shiao
*Assistant Examiner*—Janet L Coppins
(74) *Attorney, Agent, or Firm*—Kenyon & Kenyon LLP

(57) ABSTRACT

Provided is a novel crystal form of pioglitazone hydrochloride and a method for making it. Also provided is a method for making a known crystal form of pioglitazone hydrochloride.

7 Claims, 5 Drawing Sheets

PIOGLITAZONE HYDROCHLORIDE

CROSS REFERENCE TO RELATED APPLICATION

This application is a divisional of U.S. patent application Ser. No. 10/256,437, filed Sep. 27, 2002, now U.S. Pat. No. 7,135,485, which claims the benefit of U.S. Provisional Application No. 60/326,112, filed Sep. 28, 2001, the disclosures of all of which are incorporated herein by reference.

FIELD OF THE INVENTION

The present invention relates to specific crystalline forms of the antihyperglycemic compound pioglitazone hydrochloride, and to methods for producing them.

BACKGROUND

Diabetes is a disorder of metabolism in which either the pancreas produces too little or no insulin, or the body cells do not respond to the insulin that is produced. In type I diabetes, the pancreas does not produce any insulin. In type II diabetes, also known as adult onset diabetes, there are two potential problems: the pancreas produces too little insulin, or the body cells do not respond to the insulin that is produced. In either scenario, the glucose cannot efficiently move from the blood to the cells, which leads to a buildup of glucose in the blood and an overflow into the urine. As a result, the body loses its main source of fuel. Administering insulin or oral antihyperglycemic agents allows the glucose to enter the cells more efficiently, thus providing a source of fuel.

Pioglitazone is an oral antihyperglycemic agent that acts primarily by decreasing insulin resistance. Pharmacological studies indicate that pioglitazone improves sensitivity to insulin in muscle and adipose tissue and inhibits hepatic gluconeogenesis. Pioglitazone improves glucose resistance while reducing circulating insulin levels.

Pioglitazone is currently marketed as ACTOS®. Pioglitazone hydrochloride has the chemical name [(±)5-[[4-[2-(5-ethyl-2-pyridinyl)ethoxy]phenyl]methyl]-2,4-] thiazolidinedione monohydrochloride. (CAS Registry No. 111025-46-8.) The chemical structure of pioglitazone is shown as Formula I.

Formula I

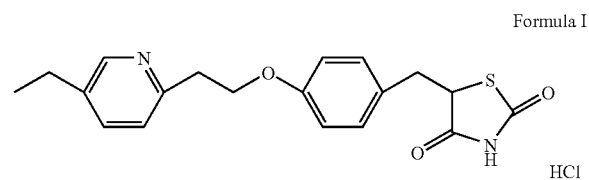

HCl

U.S. Pat. No. 5,585,495, incorporated herein by reference, discloses methods for the synthesis of pioglitazone.

SUMMARY OF THE INVENTION

The present invention provides crystalline pioglitazone hydrochloride Form II.

The present invention also provides crystalline pioglitazone hydrochloride Form II, characterized by an X-ray powder diffraction pattern having peaks at about 9.2, 10.4, 15.2, 16.4, 18.6 and 21.4±0.2 degrees two-theta.

Figure 1:
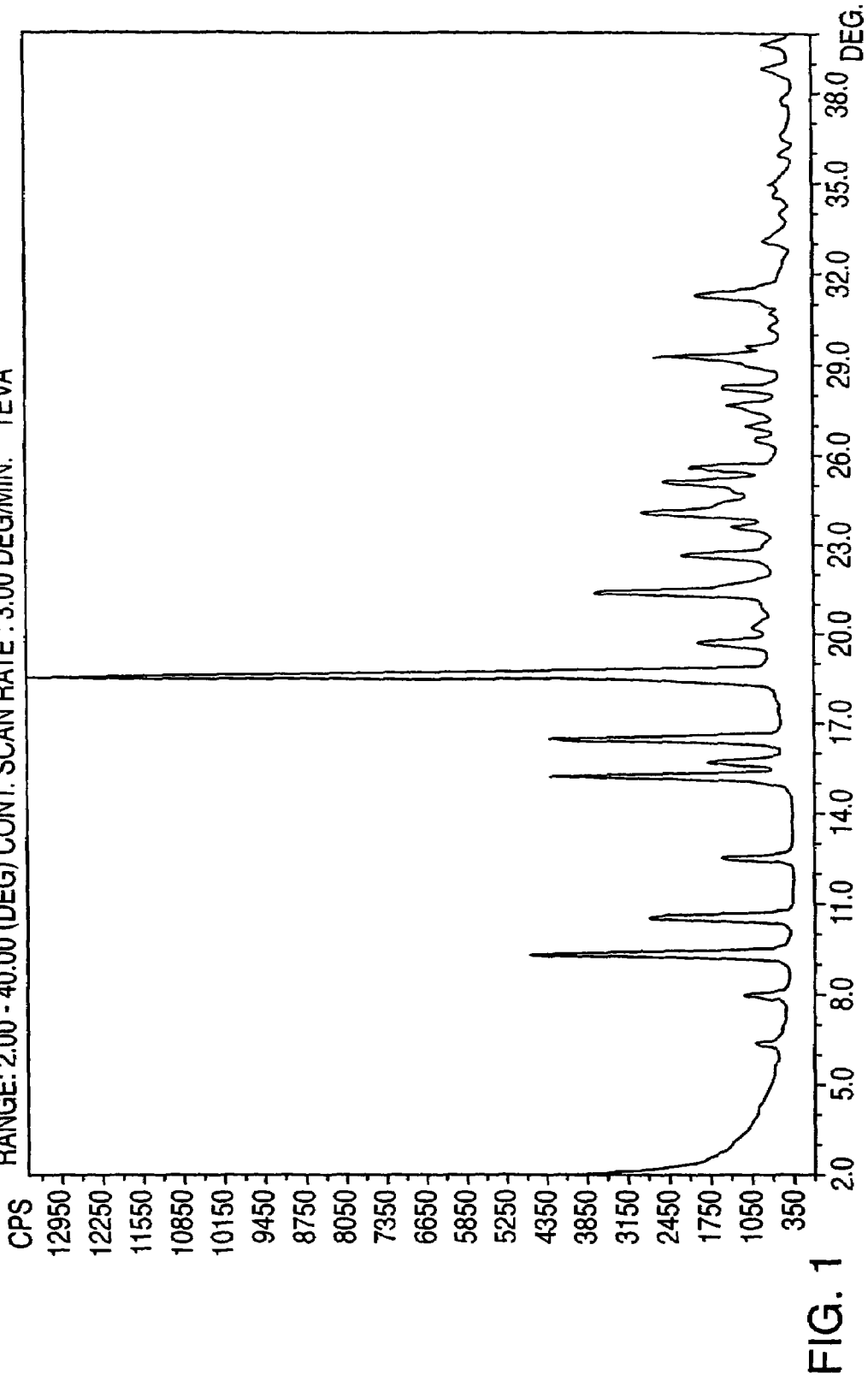
FIG. 1 shows the X-ray diffraction diagram of pioglitazone hydrochloride Form II.

The present invention also provides crystalline pioglitazone hydrochloride Form II having the X-ray powder diffraction pattern substantially as shown in FIG. 1.

The present invention also provides a pharmaceutical composition that includes crystalline pioglitazone hydrochloride Form II.

The present invention also provides a process for preparing crystalline pioglitazone hydrochloride Form II, including the steps of: dissolving pioglitazone hydrochloride in a solvent; adding water to the solution; cooling the resulting mixture and, collecting crystals of pioglitazone hydrochloride Form II.

The present invention also provides a process for preparing crystalline pioglitazone hydrochloride Form II, including the steps of: dissolving pioglitazone hydrochloride in a solvent; adding water to the solution; cooling the resulting mixture; collecting a pioglitazone hydrochloride precipitate; suspending the collected pioglitazone hydrochloride precipitate in a suspending solvent to form a slurry, collecting pioglitazone hydrochloride Form II.

The present invention further provides a process for converting crystalline pioglitazone hydrochloride Form I to pioglitazone hydrochloride Form II, including the steps of: suspending crystalline pioglitazone hydrochloride Form I in water to form a slurry and collecting crystalline pioglitazone hydrochloride Form II from the slurry.

The present invention also provides a process for preparing pioglitazone hydrochloride Form I, including the steps of: dissolving pioglitazone hydrochloride in a solubilizing solvent at a temperature above about 35° C.; cooling the solution to effect precipitation of pioglitazone hydrochloride; and collecting pioglitazone hydrochloride Form I.

The present invention also provides a process for preparing crystalline pioglitazone hydrochloride Form I, including the steps of: dissolving pioglitazone hydrochloride in a solubilizing solvent at elevated temperature; adding an anti-solvent to the solution; cooling the mixture of solution and anti-solvent; and collecting pioglitazone hydrochloride Form I.

DETAILED DESCRIPTION OF THE INVENTION

The present invention provides new crystal forms of pioglitazone hydrochloride. The discovery of a new crystalline form of a pharmaceutically useful compound provides an opportunity to improve the performance characteristics of a pharmaceutical product. It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new crystalline forms of a useful compound. For a general review of polymorphs and the pharmaceutical applications of polymorphs consult G. M. Wall, *Pharm Manuf.* 3, 33 (1986); J. K. Haleblian and W. McCrone, *J. Pharm. Sci.*, 58, 911 (1969); and J. K. Haleblian, *J. Pharm. Sci.*, 64, 1269 (1975), all of which are incorporated herein by reference.

The present invention relates to the solid state forms (i.e. polymorphs and pseudopolymorphs) of pioglitazone hydrochloride that can be prepared by any of the methods herein described. The polymorphs and pseudopolymorphs can be influenced by controlling the conditions under which the hydrochloride salt is obtained in solid form. Solid state physical properties that can differ from one polymorph to the next include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate.

Another important solid state property of a pharmaceutical compound that can depend on crystal structure is its rate of dissolution in aqueous media. The rate of dissolution of an active ingredient in a patient's stomach fluid can have therapeutic consequences because it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics can be influenced by the conformation and orientation of molecules in the unit cell, which defines a particular polymorphic form of a substance. The polymorphic form may give rise to thermodynamic properties that are different from those of the amorphous material or another polymorphic form. Thermodynamic properties can be used to distinguish between polymorphs and pseudopolymorphs. Thermodynamic properties that can be used to distinguish between polymorphs can be measured in the laboratory by such techniques as capillary melting point, thermogravimetric analysis (TGA), differential scanning calorimetry (DSC), and differential thermal analysis (DTA).

A particular polymorphic form can also possess distinct spectroscopic properties that may be detectable by, for example, solid state $^{13}C$ NMR spectroscopy and infrared (IR) spectroscopy.

X-ray crystallography on powders (powder diffractometry) can be used to obtain x-ray diffraction diagrams that reveal information on the crystal structure of different polymorphs and pseudopolymorphs.

As used herein, room temperature means a temperature from about 20° C. to about 25° C.

As used herein in connection with a measured quantity, about refers to the normal variation in that measured quantity as expected by the skilled artisan making the measurement and exercising a level of care commensurate with the objective of the measurement and the precision of the measuring equipment.

All powder X-ray diffraction patterns were obtained by methods known in the art using a Scintag X'TRA X-ray powder diffractometer, equipped with a solid state Si(Li) detector thermoelectrically cooled, at scanning speed of 3° min.$^{-1}$ over the scanning range 2-40 degrees two-theta. Copper radiation of $\lambda$=1.5418 Å was used.

The DTA and TGA thermograms presented herein were obtained by methods known in the art using a DTG Shimadzu model DTG-50; which provides combined TGA and DTA thermograms. TGA traces reflect transitions that involve either a loss or gain of mass. DTA gives information on, for example, first and second-order thermodynamic transitions in the sample. The weight of the samples for thermal analysis was between about 9 and about 13 mg. The samples were scanned up to about 250° C. or above at a rate of 10° C./min. Sample chambers were purged with nitrogen gas at a flow rate of 20 ml/min. Standard alumina crucibles were used.

Differential scanning calorimetric thermograms were obtained with a Mettler Toledo DSC 321$^e$ system. Samples of 3 mg to 5 mg contained in aluminum crucibles with three-hole covers were scanned at a heating rate of 10° per minute.

Karl Fisher analysis, which is well known in the art, can be used to determine the quantity of water in a sample.

The term "equivalents of water" means molar equivalents of water.

All percentages herein are by weight unless otherwise indicated.

As used herein, a solvent is any liquid substance capable of dissolving an organic compound such as pioglitazone. As used herein, the term "anti-solvent" means a liquid in which an organic compound such as pioglitazone is poorly soluble. Combining an anti-solvent with a solvent reduces the solubility of a compound in the combination relative to its solubility in solvent alone. As used herein, a mixture of solvents refers to a composition including more than one solvent.

As used herein, the term "pioglitazone hydrochloride" means pioglitazone hydrochloride in any form including anhydrous forms, hydrates, and solvates of pioglitazone hydrochloride.

Pioglitazone can be synthesized as disclosed in U.S. Pat. Nos. 5,952,509 and 5,585,495.

Pioglitazone Hydrochloride Form I

Figure 4:
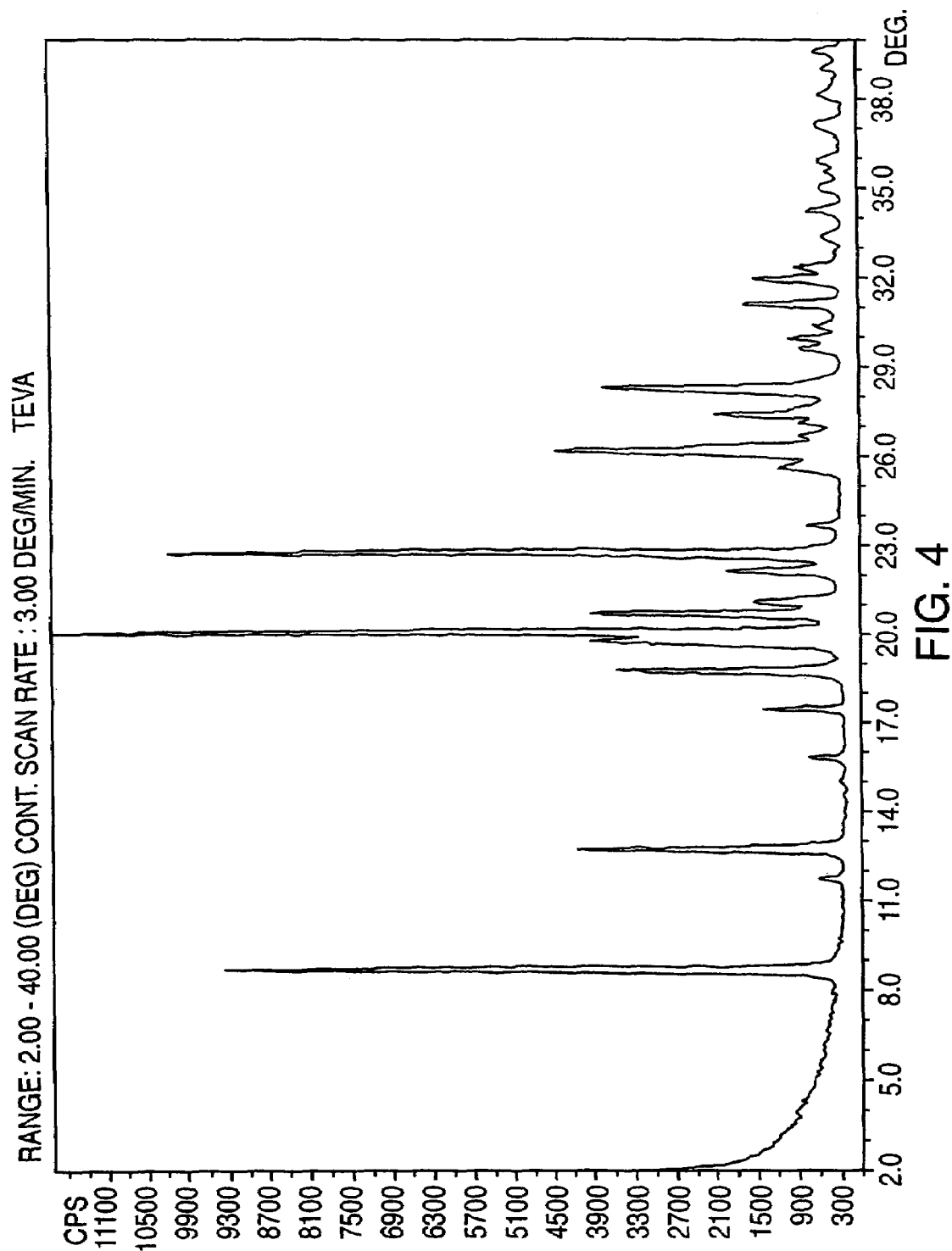
FIG. 4 shows the X-ray diffraction diagram for prior art pioglitazone hydrochloride Form I.
Figure 5:
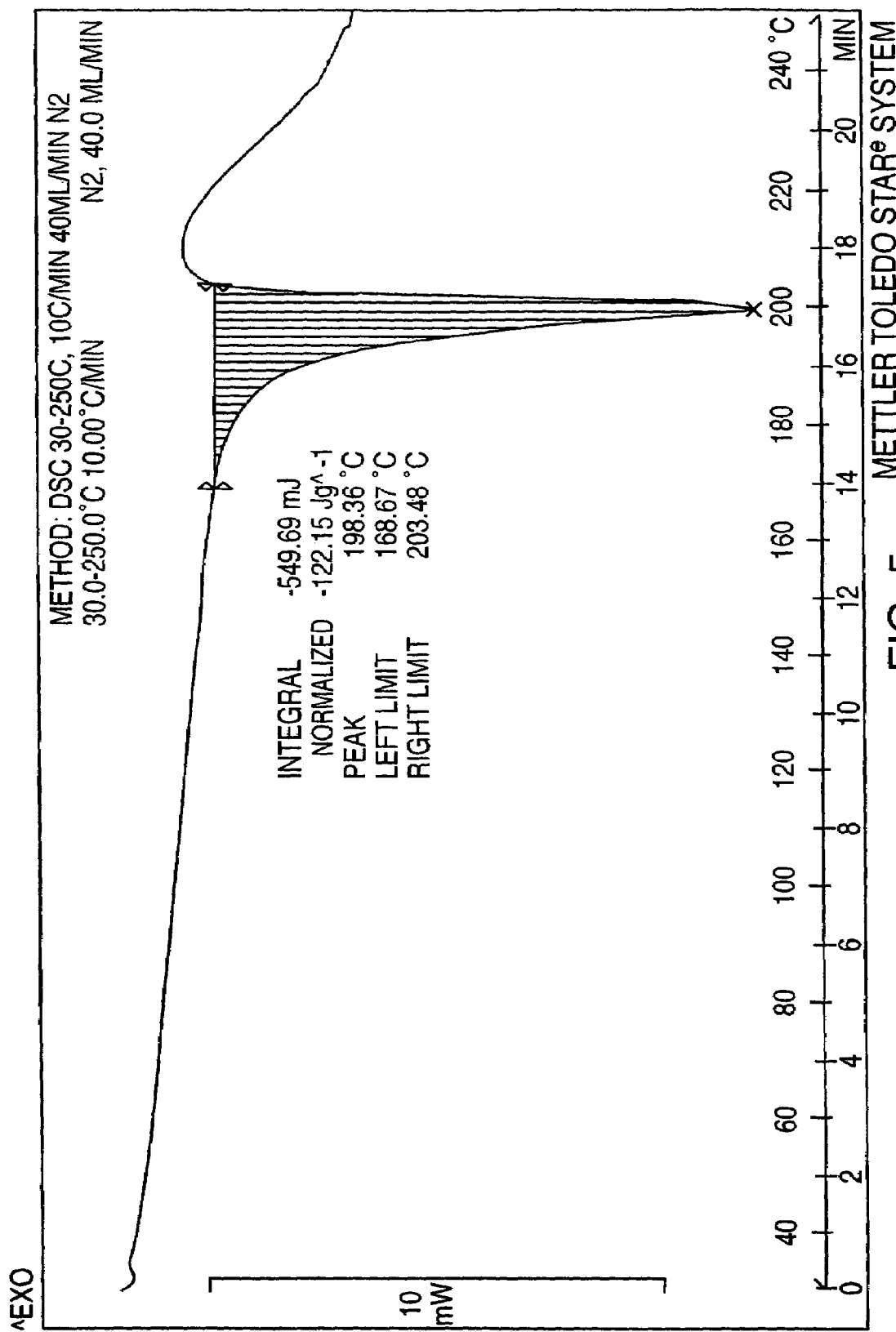
FIG. 5 shows a DSC thermogram of prior art pioglitazone hydrochloride Form I.

Pioglitazone hydrochloride Form I ("Form I") is the prior art anhydrous form of pioglitazone hydrochloride. The DSC thermogram and x-ray powder difraction diagram for a typical sample of prior art Form I pioglitazone hydrochloride are shown in FIGS. 5 and 4, respectively.

Pioglitazone Hydrochloride Form II

Crystalline pioglitazone hydrochloride Form II ("Form II") is characterized by an X-ray diffraction pattern having peaks (reflections) at about 2θ=9.2, 10.4, 15.2, 16.4, 18.6 and 21.4±0.2. A typical x-ray powder diffraction diagram of Form II is shown in FIG. 1.

Figure 2:
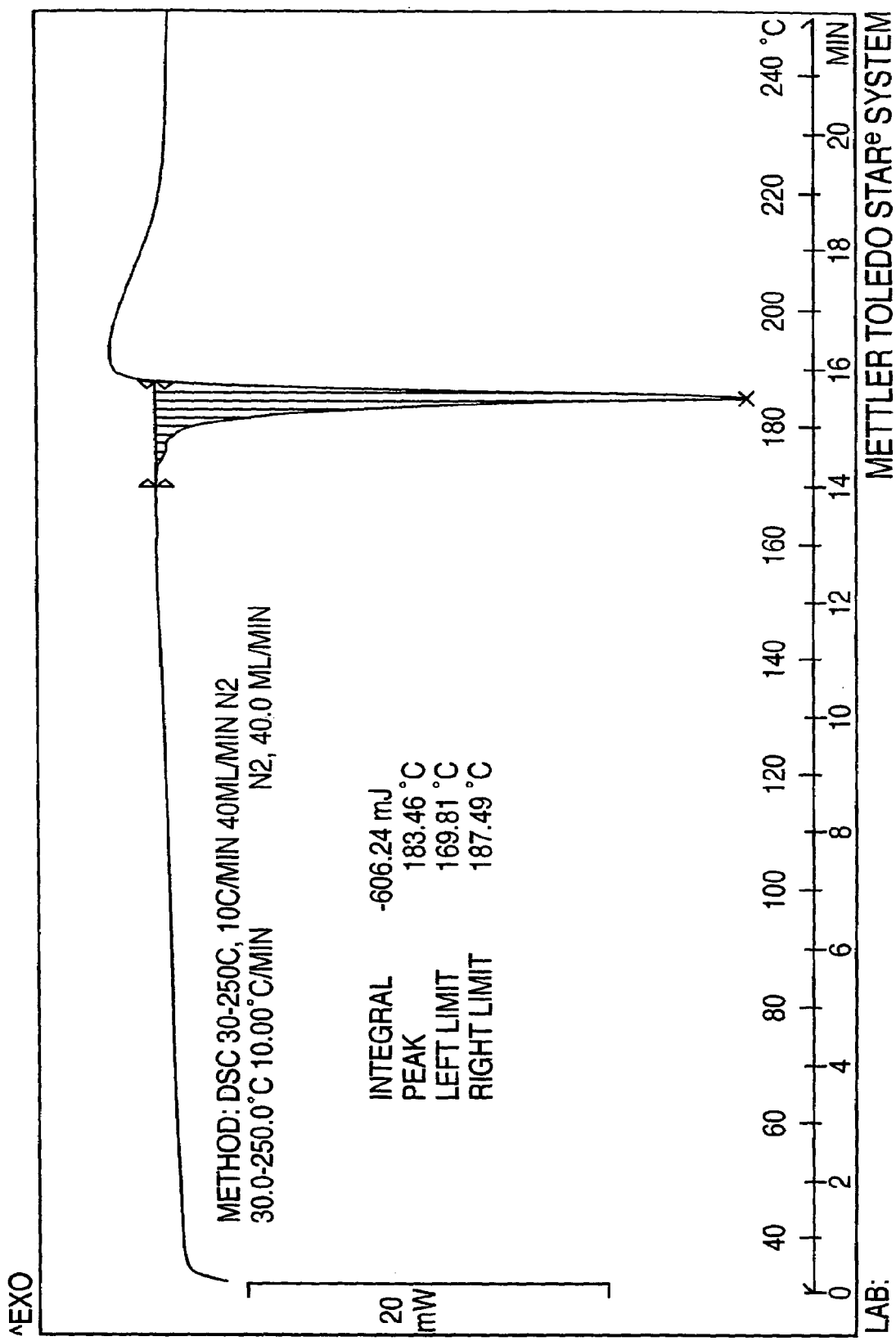
FIG. 2 shows a DSC thermogram of pioglitazone hydrochloride Form II.
Figure 3:
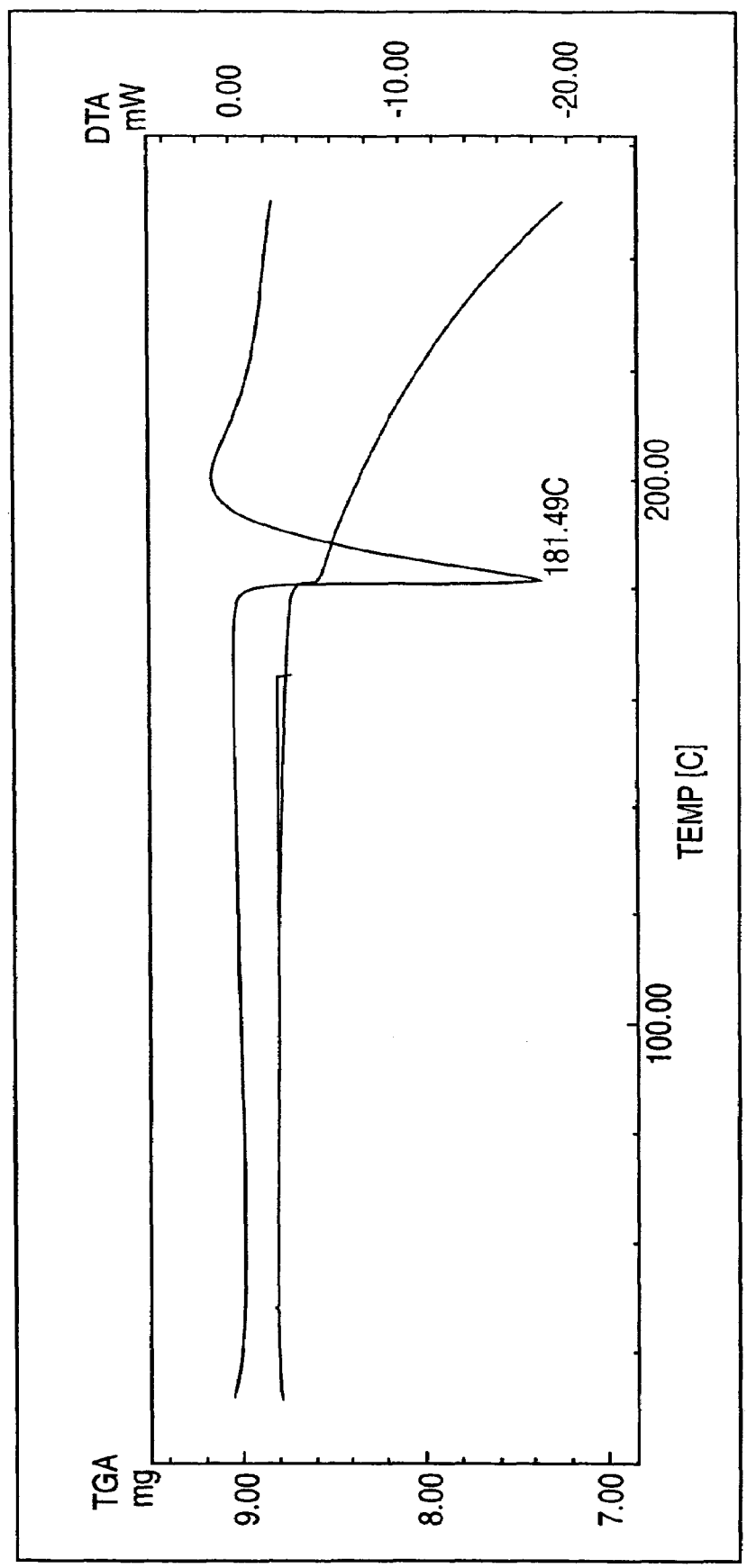
FIG. 3 shows a DTG thermogram of pioglitazone hydrochloride Form II.

The DSC and DTA thermograms of Form II pioglitazone hydrochloride are characterized by an endothermic peak at about 180° C. The DSC thermogram of a typical sample of Form II is shown in FIG. 2. The combined DTA-TGA profile of a typical sample of Form II pioglitazone hydrochloride is shown in FIG. 3. The decomposition of the sample in this temperature range is demonstrated by the sharp weight loss recorded by TGA. No significant weight loss occurs up to this temperature.

Procedures for Obtaining Polymorphs of Pioglitazone Hydrochloride

The novel forms of crystalline pioglitazone hydrochloride disclosed herein can be formed by crystallization from a solvent, optionally with the aid of an anti-solvent. Novel forms of crystalline pioglitazone hydrochloride disclosed herein can also be formed by suspending crystals of pioglitazone hydrochloride as a slurry in a suspending solvent. It will be understood by those of skill in the art that other methods may also be used to form the polymorphs disclosed herein.

In one embodiment, the present invention provides a crystallization process for preparing crystalline pioglitazone hydrochloride Form II, including the steps of: dissolving pioglitazone hydrochloride in a solubilizing solvent to form a solution having a concentration between about 0.01 g/ml to about 0.15 g/ml.; adding water to the solution (ca. 0.9 to 2 ml. water per ml. solution); cooling the resulting mixture to a temperature of about −4° C. to obtain a slurry; and collecting crystals of pioglitazone hydrochloride Form II in about 70% yield.

The dissolution can be at room temperature, or it can be at elevated temperature, for example from about 35° C. to about 70° C. Preferably, dissolution is at elevated temperature When dissolution is at elevated temperature, the cooling step can consist, and preferably does consist, of first exposing the slurry to room temperature for about 3 hours and then cooling the slurry to about 4° C. and maintaining it at this temperature for about 15 to about 18 hours.

Suitable solubilizing solvents for making Form II according to this embodiment include dimethylformamide, N,N-dimethylacetamide, acetic acid, dimethyl sulfoxide, and ethylene glycol.

In another embodiment, the crystallization process can be followed by a slurry or trituration step. In this case, the pioglitazone collected from the cooled mixture of solution and water is suspended in a suspending solvent (ca. 1 mL. suspending solvent per gram solid) to form a slurry from which pioglitazone hydrochloride Form II is collected.

Acetone, methanol, ethanol, methyl tert-butyl ether, chloroform, dichloromethane, about 96% ethanol, ethyl acetate, methyl ethyl ketone, isopropyl alcohol butylacetate, and water are useful as suspending solvents for the slurry step.

In yet another embodiment, the present invention provides an aqueous suspension—or slurry—process for converting crystalline pioglitazone hydrochloride Form I to pioglitazone hydrochloride Form II, including the steps of: suspending crystalline pioglitazone hydrochloride Form I in water to form a slurry (ca. 5 mL. to 50 mL water per gram of Form I) and collecting crystalline pioglitazone hydrochloride Form II from the slurry. As used herein, slurrying is mixing a liquid (i.e. a suspending solvent) with solid particles.

In still another embodiment, the present invention provides a process for preparing pioglitazone hydrochloride Form I, including the steps of: dissolving pioglitazone hydrochloride in a solubilizing solvent selected from the group consisting of dimethylformamide, methanol, acetic acid, N,N,-dimethylacetamide, and ethylene glycol (ca. 0.01 mL to 0.15 mL solubilizing solvent per gram) at elevated temperature greater than room temperature, preferably at a temperature greater that 35 C, most preferably from about 60° C. to about 65° C., to form a solution; cooling the solution to obtain a slurry; and collecting pioglitazone hydrochloride Form I from the slurry.

In the last recited embodiment, the cooling step can and preferably does consist of first cooling the slurry at room temperature for about 3 hours and then cooling the slurry to about 4° C. and maintaining it at this temperature for about 15 to about 18 hours.

In still another embodiment, the present invention provides a process for preparing crystalline pioglitazone hydrochloride Form I, including the steps of: dissolving pioglitazone hydrochloride in a solubilizing solvent, (ca. 0.01 mL to 0.15 mL per gram) at elevated temperature to form a solution; mixing an anti-solvent with the solution; cooling the mixture of solution and anti-solvent to obtain a slurry; and collecting pioglitazone hydrochloride Form I therefrom. Preferably, dissolution is at a temperature greater that about 35 C.

Suitable solubilizing solvents include dimethylformamide, dimethyl sulfoxide, N,N-dimethylacetamide, and acetic acid. When the solubilizing solvent is selected from dimethylformamide, N,N-dimethylacetamide, or dimethyl sulfoxide, suitable anti-solvents include methyl ethyl ketone, absolute ethanol, ethyl acetate, butanol and acetone. Ethyl acetate can be used as anti-solvent when dimethylformamide is the solubilizing solvent. When acetic acid is the solubilizing solvent, butanol and dioxane are suitable anti-solvents. i-Propyl alcohol is a suitable anti-solvent when either N,N-dimethylacetamide or acetic acid is the solubilizing solvent.

In the above embodiment, when dissolution is at an elevated temperature, the cooling step can and preferably does consist of first cooling the slurry at room temperature for about 3 hours and then cooling the slurry to about 4° C. and maintaining it at this temperature for about 15 to about 18 hours.

Methods of Use, Formulations, Dosages

Pioglitazone hydrochloride Forms I and II may be formulated into a variety of pharmaceutical compositions and dosage forms that are useful in treating patients afflicted with type II diabetes.

Pharmaceutical compositions of the present invention contain pioglitazone hydrochloride Forms I and II, optionally in mixture with each other. Pharmaceutical compositions of the present invention also may contain other pioglitazone hydrochloride crystalline forms, amorphous pioglitazone hydrochloride and/or other active ingredients in mixture with one or more of pioglitazone hydrochloride Forms I and II. In addition to the active ingredient(s), pioglitazone hydrochloride pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and caregiver to handle. Diluents for solid compositions include, for example, microcrystalline cellulose (e.g. AVICEL®, microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelitinized starch, sodium alginate and starch. The dissolution rate of a compacted solid pharmaceutical composition in the patient's stomach may be increased by the addition of a disintegrant to the composition.

Disintegrants include alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flow properties of non-compacted solid compositions and improve the accuracy of dosing. Excipients that may function as glidants include colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges as well as liquid syrups, suspensions and elixirs. An especially preferred dosage form of the present invention is a tablet.

The currently marketed form of pioglitazone (ACTOS®) is available as a tablet for oral administration containing 15 mg, 30 mg, or 45 mg of pioglitazone (as the base) formulated with the following excipients: lactose monohydrate, NF, hydroxypropylcellulose NF, carboxymethylcellulose calcium NF, and magnesium stearate NF.

The function and advantage of these and other embodiments of the present invention will be more fully understood from the non-limiting examples below. The following examples are intended to illustrate the benefits of the present invention, but do not exemplify the full scope of the invention.

In each example, the polymorphic form of the pioglitazone hydrochloride obtained was confirmed by DSC and x-ray diffraction.

EXAMPLES

Example 1

Preparation of Pioglitazone Hydrochloride Form II

Pioglitazone hydrochloride (4 g.) was dissolved in acetic acid portionwise until complete dissolution at 35° C. (total solvent 40 mL). Water (75 mL) was then added portionwise at this temperature with stirring until the solution became turbid and crystallization began. The solution was allowed to cool at room temperature for 3 hours, then cooled to 4° C. and maintained at this temperature for 16 hours The crystals so formed were then recovered on a Buchner funnel and left to dry for 5 minutes on the funnel.

Example 2

Preparation of Pioglitazone Hydrochloride Form II

Pioglitazone hydrochloride (4 g.) was dissolved in ethylene portionwise until complete dissolution at 35° C. (total volume solvent @@@@ ml.). Water (@@@@ ml.) was then added portionwise at this temperature with stirring until the solution became turbid and crystallization started. The solution was allowed to cool at room temperature for 3 hours, and then cooled to 4° C. and maintained at this temperature for @@@@ hours.

The crystals were then collected on a Buchner funnel with moderate vacuum (50-100 mm. Hg), and left to dry for 5 minutes under these conditions.

Example 3

Preparation of Pioglitazone Hydrochloride Form II

Pioglitazone hydrochloride (4.) was dissolved in acetic acid portionwise until complete dissolution at 35° C. (total volume solvent 115 mL Water (220 mL) s then added portionwise at this temperature; with stirring, until the solution became turbid and crystallization began. The solution was allowed to cool at room temperature for 3 hours, and then cooled to 4° C. and maintained at this temperature for @@@@ hours. The crystals were then collected on a Buchner funnel with moderate suction (50-100 mm vacuum), and left to dry for 5 minutes under these conditions.

Example 4

Preparation of Pioglitazone Hydrochloride in Form II 50 g. of pioglitazone hydrochloride were dissolved in 120 ml. of dimethylformamide with stirring at about 35° C. Water (150 ml.) was added and the solution became turbid. The mixture was allowed to stand at room temperature for several hours, then at 4° C. overnight. The crystals were filtered off and dried to constant weight at 45° C. under vacuum.

A portion of the resulting pioglitazone hydrochloride crystals (1.5 g.) was suspended in 10 ml. acetone to form a slurry. The slurry was stirred for 48 hours at room temperature, then the crystals were collected by filtration. The collected crystals were dried at 40° C./100 mm. Hg for 72 hours.

Example 5

Preparation of Pioglitazone Hydrochloride Form II 50 g. of pioglitazone hydrochloride were dissolved in 120 ml. of dimethylformamide with stirring at about 35° C. Water (150 ml.) was added until the solution became turbid. The mixture was left at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml. methanol. The mixture was stirred for 48 hours at room temperature, then the crystals were collected by filtration. The crystals were dried at 40° C./100 mm. Hg for 72 hours.

Example 6

Preparation of Pioglitazone Hydrochloride Form II 50 g. of pioglitazone hydrochloride were dissolved in 120 ml. of dimethylformamide with stirring at about 35° C. Water (150 ml.) was added and the solution became turbid. The mixture was allowed to stand at room temperature for several hours, then at 4° C. overnight. The crystals were collected by filtration and dried to constant weight at 45° C. under vacuum.

A portion (1.5 g.) of the resulting pioglitazone hydrochloride crystals was suspended in 10 ml. absolute ethanol. The slurry was stirred for 48 hours at room temperature, then the crystals were filtered off. The crystals were dried at 40° C./100 mm Hg for 72 hours.

Example 7

Preparation of Pioglitazone Hydrochloride Form II 50 g. of pioglitazone hydrochloride were dissolved in 120 ml. of dimethylformamide with stirring about 35° C. Water (150 ml.) was added and the solution became turbid. The mixture was allowed to stand at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml methyl t-butyl ether. The mixture was stirred for 48 hours at room temperature, then the crystals were filtered off. The crystals were dried at 40° C./100 mm. Hg for 72 hours.

Example 8

Preparation of Pioglitazone Hydrochloride Form II 50 g of pioglitazone hydrochloride were dissolved in 120 ml. of dimethylformamide with stirring at about 35° C. Water (150 ml.) was added and the solution became turbid. The mixture was allowed to stand at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml. chloroform to form a slurry. The slurry was stirred for 48 hours at room temperature, then the crystals were collected by filtration. The crystals were dried at 40° C./100 mm. Hg for 72 hours.

Example 9

Preparation of Pioglitazone Hydrochloride Form II 50 g. of pioglitazone hydrochloride were dissolved in 120 ml. of dimethylformamide with stirring about 35° C. Water (150 ml.) was added and the solution became turbid. The mixture was allowed to stand at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml. dichloromethane. The slurry was stirred for 48 hours at room temperature, then the crystals were collected by filtration. The crystals collected were dried at 40° C./100 mm. Hg for 72 hours.

Example 10

Preparation of Pioglitazone Hydrochloride Form II 50 g. of pioglitazone hydrochloride were dissolved in 120 ml. of dimethylformamide with stirring at about 35° C. Water (150 ml.) was added and the solution became turbid. The mixture was left at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml. of 96% ethanol. The slurry was stirred for 48 hours at room temperature, then the crystals were collected by filtration. The crystals were dried at 40° C./100 mm. Hg for 72 hours.

Example 11

Preparation of Pioglitazone Hydrochloride Form II 50 g. of pioglitazone hydrochloride were dissolved in 120 ml. of dimethylformamide with stirring at about 35° C. Water (150 ml.) was added and the solution became turbid. The mixture was left at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml. ethyl acetate. The slurry was stirred for 48 hours at room temperature, then the crystals were collected by filtration. The crystals were dried at 40° C./100 mm. Hg for 72 hours.

Example 12

Preparation of Pioglitazone Hydrochloride Form II 50 g. of pioglitazone hydrochloride were dissolved in 120 ml. of dimethylformamide with stirring at about 35° C. Water (150 ml.) was added until the solution became turbid. The mixture was left at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml methyl ethyl ketone. The slurry was stirred for 48 hours at room temperature, then the crystals were collected by filtration. The crystals were dried at 40° C./100 mm. Hg for 72 hours.

Example 13

Preparation of Pioglitazone Hydrochloride Form II 50 g. of pioglitazone hydrochloride were dissolved in 120 ml. of dimethylformamide with stirring at about 35° C. and 150 ml. of water was added until the solution became turbid. The mixture was left at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml. isopropyl alcohol. The slurry was stirred for 48 hours at room temperature, then the crystals were collected by filtration. The crystals were dried at 40° C./100 mm. Hg for 72 hours.

Example 14

Preparation of Pioglitazone Hydrochloride Form II 50 g. of pioglitazone hydrochloride were dissolved in 120 ml. of dimethylformamide with stirring about 35° C. Water (150 ml.) was added and the solution became turbid. The mixture was left at room temperature for several hours then at 4° C. overnight. The crystals were collected by filtration and dried to constant weight at 45° C. under vacuum.

A portion (1.5 g.) of the resulting pioglitazone hydrochloride crystals was suspended in 10 ml. butyl acetate. The slurry was stirred for 48 hours at room temperature, then the crystals were collected by filtration. The crystals were dried at 40° C./100 mm. Hg for 72 hours.

Example 15

Conversion of Form I to Form II

A 50 ml. flask was charged with 1.5 g. of pioglitazone hydrochloride Form 1 and 10 ml. of water. The suspension was stirred for 48 hours at room temperature, then the crystals were collected by filtration.

Example 16

Three grams of pioglitazone hydrochloride Form I were combined with 5 mL of a 1:1.3 (v/v) mixture of dimethyl formamide and water. The resulting mixture was mechanically agitated for about 120 hours.

Example 17a through 17e

Preparation of Form I by Crystallization from a Solvent

In each case, 4 g. of pioglitazone hydrochloride were added portion-wise, with stirring, to a quantity of solvent. The resulting mixture was stirred at 65° C. until dissolution was complete. The solution was left to cool at room temperature for 3 hours, then at 4° C. for 18 hours. Crystals of Form I were then recovered by crystallization. The kind and amount of solvent used in each experiment is listed in Table I.

TABLE I

Solvents for Preparing Pioglitazone Form I by Crystallization

| SOLVENTS | RATIO (w/v) OF FORM I TO SOLVENT |
|---|---|
| dimethylformamide | @@@@@@ |
| methanol | 1:5 |
| N,N,-dimethylacetamide | 1:5 |
| Acetic acid | 1:7.25 |
| Ethylene glycol | 1:3.75 |

Example 18A through 18Q

Preparation of Form I by Crystallization Using a Solvent/Anti-Solvent Pair

The following general procedure was followed in each of examples 18A through 18Q.

The desired amount of pioglitazone hydrochloride was dissolved in the chosen solvent at 35° C. A corresponding anti-solvent was then added portionwise at 35° C., with stirring, until the solution became turbid and crystallization began. The mixture was stirred at room temperature for 3 hours, then cooled to 4° C. and maintained at that temperature for 18 hours. The crystals that formed were collected by filtration.

The kinds and amount of solvent and anti-solvent for each experiment are given in Table II.

TABLE II

Solvents for Preparing Pioglitazone Form I from a Binary Solvent System

| EXPERIMENT | SOLVENT/ANTI-SOLVENT | RATIO OF SOLVENT:ANTI-SOLVENT | RATIO OF SOLID TO SOLVENT |
|---|---|---|---|
| 18A | Dimethylformamide/Ethyl acetate | 1:0.15 | 1:5.8 |
| 18B | Dimethylformamide/Methyl ethyl ketone | 1:3.8 | 1:23.8 |
| 18C | Dimethylformamide/Ethanol (abs.) | 1:5 | 1:30 |
| 18D | Dimethylformamide/Acetone | 1:1.3 | 1:11.3 |
| 18E | Dimethylsulfoxide/Methyl ethyl ketone | 1:10 | 1:27.5 |
| 18F | MeOH/Methyl ethyl ketone | 1:2.7 | 1:42 |
| 18G | MeOH/Ethyl acetate | 1:1.1 | 1:23.8 |
| 18H | MeOH/Butanol | 1:2.2 | 1:36.3 |
| 18I | N,N,-dimethylacetamide/Isopropanol | 1:1.7 | 1:20 |
| 18J | N,N,-dimethylacetamide/Ethyl acetate | 1:1 | 1:15 |
| 18K | N,N,-dimethylacetamide/Acetone | 1:2.4 | 1:25.8 |
| 18L | N,N,-dimethylacetamide/methyl ethyl ketone | 1:2.5 | 1:26.3 |
| 18M | Dimethylsulfoxide/Ethanol (abs.) | 1:1 | 1:5 |
| 18N | Dimethylsulfoxide/Acetone | 1:7.5 | 1:21.3 |
| 18O | Acetic acid/Isopropanol | 1:1.25 | 1:22.5 |

TABLE II-continued

Solvents for Preparing Pioglitazone Form I from a Binary Solvent System

| EXPERI-MENT | SOLVENT/ANTI-SOLVENT | RATIO OF SOLVENT:ANTI-SOLVENT | RATIO OF SOLID TO SOLVENT |
|---|---|---|---|
| 18P | Acetic acid/Butanol | 1:2.8 | 1:37.5 |
| 18Q | Acetic acid/Dioxane | 1:1.25 | 1:22.5 |

We claim:

1. A method for making pioglitazone hydrochloride in Form I, having an X-ray diffraction pattern characterized by major peaks at about 8.7, 12.9, 19.8, 20.1, 20.8, 22.9, 26.2, 27.5, and 28.4±0.2 degrees two theta, and a DSC thermogram characterized by a peak at 195° C. when heated at 10° C. per minute, comprising the steps of:
   a) dissolving pioglitazone hydrochloride in a solubilizing solvent selected from dimethyl formamide, dimethyl acetamide, acetic acid to form a solution,
   b) cooling the solution whereby a precipitate forms, and
   c) collecting pioglitazone hydrochloride Form I.

2. The method of claim 1 wherein the dissolving is at a temperature greater than about 35° C.

3. The method of claim 2 wherein the pioglitazone hydrochloride is dissolved at a temperature between about 60° C. and 65° C.

4. The method of claim 2 wherein the cooling is effected in two steps: first to room temperature, and second, to about 4° C.

5. A method for making pioglitazone hydrochloride in Form I, having an X-ray diffraction pattern characterized by major peaks at about 8.7, 12.9, 19.8, 20.1, 20.8, 22.9, 26.2, 27.5, and 28.4±0.2 degrees two theta, and a DSC thermogram characterized by a peak at 195° C. when heated at 10° C. per minute, comprising the steps of:
   a) dissolving pioglitazone hydrochloride in a solubilizing solvent selected from dimethyl formamide and dimethyl sulfoxide at a temperature between about 35° C. and 65° C. to form a solution,
   b) mixing the solution with an anti-solvent,
   c) cooling the mixture of solution and anti-solvent whereby a precipitate forms, and
   d) collecting pioglitazone hydrochloride Form I.

6. The method of claim 2 wherein the anti-solvent is selected from the group consisting of ethyl acetate, methyl ethyl ketone, absolute ethanol, and acetone.

7. The method of claim 2 wherein the cooling is effected in two steps: first to room temperature, and second, to about 4° C.

* * * * *